United States Patent
Melodelima et al.

(10) Patent No.: US 9,737,324 B2
(45) Date of Patent: Aug. 22, 2017

(54) THERAPEUTIC PROBE FOR TREATING TISSUE USING FOCUSED INTERSECTING ULTRASONIC WAVES

(75) Inventors: David Melodelima, Ruy (FR); Jeremy Vincenot, Les Haies (FR); Emmanuel Blanc, Saint-Didier Au Mont d'Or (FR); Jean-Yves Chapelon, Villeurbanne (FR)

(73) Assignees: EDAP TMS FRANCE, Vaulx-en-Velin (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 595 days.

(21) Appl. No.: 14/007,333

(22) PCT Filed: Mar. 15, 2012

(86) PCT No.: PCT/FR2012/050546
§ 371 (c)(1),
(2), (4) Date: Dec. 3, 2013

(87) PCT Pub. No.: WO2012/131213
PCT Pub. Date: Oct. 4, 2012

(65) Prior Publication Data
US 2014/0081300 A1    Mar. 20, 2014

(30) Foreign Application Priority Data
Mar. 29, 2011    (FR) ...................................... 11 52600

(51) Int. Cl.
*A61B 17/32*    (2006.01)
*A61N 7/02*    (2006.01)
(Continued)

(52) U.S. Cl.
CPC ........ *A61B 17/320068* (2013.01); *A61N 7/02* (2013.01); *A61B 2090/378* (2016.02);
(Continued)

(58) Field of Classification Search
CPC .... A61N 2007/0065; A61N 2007/0078; A61N 2007/027; A61N 7/02; A61B 17/320068; A61B 2090/378
See application file for complete search history.

(56) References Cited

U.S. PATENT DOCUMENTS

2008/0194955 A1*   8/2008   Lacoste .................... A61N 7/02
                                                    600/439
2009/0230823 A1*   9/2009   Kushculey ............... A61N 7/02
                                                    310/366

FOREIGN PATENT DOCUMENTS

WO    2006021651 A1    3/2006
WO    2010029556 A1    3/2010

OTHER PUBLICATIONS

International Search Report mailed Jul. 13, 2012, corresponding to PCT/FR2012/050546.
(Continued)

*Primary Examiner* — Richard Louis
(74) *Attorney, Agent, or Firm* — Ladas & Parry LLP (57) ABSTRACT

A therapeutic probe having a transducer for focusing the ultrasonic waves into a first focal area, the emission surface of which has, within a profile plane, two concave curve segments which have a finite length and which are symmetrical relative to a plane of symmetry, or to an axis of symmetry. Within the profile plane, both concave curve segments extend along arcs of first and second non-coincident circles that intersect each other, and each curve segment has an acoustic axis intersecting the axis of symmetry, or the plane of symmetry, between the first focal area and the emission surface, the acoustic axes being spaced apart from
(Continued)

each other such that the beams from the emission surface intersect each other so as to create a second focal area located in and situated between the first focal area and the emission surface.

8 Claims, 6 Drawing Sheets

(51) Int. Cl.
 *A61N 7/00* (2006.01)
 *A61B 90/00* (2016.01)
(52) U.S. Cl.
 CPC ................ *A61N 2007/0065* (2013.01); *A61N 2007/0078* (2013.01); *A61N 2007/027* (2013.01)

(56) References Cited

OTHER PUBLICATIONS

M. William Apoutou N'Djin. "Transducteur torique a Ultrasons Focalises de Haute Intensite pour generer des ablations volumineuses." Dec. 17, 2008.

* cited by examiner

THERAPEUTIC PROBE FOR TREATING TISSUE USING FOCUSED INTERSECTING ULTRASONIC WAVES

This application is a 371 of PCT/FR2012/050546, filed on Mar. 15, 2012, which claims priority to French Patent Application No. 1152600, filed Mar. 29, 2011.

The present invention relates to the technical field of apparatuses or devices including an ultrasonic probe formed by a plurality of ultrasonic transducer elements, suitable for emitting high intensity focused ultrasounds (HIFU).

The subject-matter of the present invention is particularly advantageously applicable in the field of therapeutic treatments using focused ultrasonic waves.

It is known that focused ultrasonic wave therapy makes it possible to create biological lesions in tissue resulting from a combination of the thermal effects and the acoustic cavitation activity. The shape of these tissue lesions results directly from the shape of the emission surface of the ultrasonic probe used.

For example, the natural geometric focusing of a traditional spherical HIFU ultrasonic transducer is periodic, but due to geometric aberrations, the focal area has an ellipsoid shape. Likewise, a toroid-shaped HIFU transducer leads to obtaining a focal area in the shape of a ring or crown.

Irrespective of the shape of the ultrasonic transducer, it should be considered that the more focused the ultrasonic transducer is, the better the spatial resolution of the focal area and the biological lesion will be. This results in preserving the tissue adjacent to that situated in the focal area, leading to a reduced lesion volume and therefore longer treatment time.

To reduce the treatment time, the volume of the biological lesion resulting from the application of each of the ultrasonic pulses should be increased. To that end, different solutions may be considered. For example, it may be provided to increase the focal volume by reducing the opening of the ultrasonic transducer. However, in such a case, the acoustic pressure gradient on the path of the ultrasonic wave is also reduced, and the intermediate tissue areas between the transducer and the focal area are then exposed to greater heating.

Another solution consists of increasing the focal volume by reducing the operating frequency. However, reducing the frequency of the ultrasonic waves also causes a reduction in the absorbed energy, and therefore the heat deposition in the tissue.

It may also be considered to increase the acoustic power emitted by the ultrasonic transducer. However, the areas of the tissue situated between the focal area and the transducer are then exposed to more intense acoustic powers that may lead to lesions outside the targeted area.

U.S. Pat. No. 5,873,845 proposes another solution consisting of placing a refractory lens in front of the ultrasonic transducer so as to widen the focal area. Although this solution is simple and inexpensive, it offers limited performance and the lens absorbs part of the emitted acoustic energy.

Patent EP 0,214,782 describes another solution relative to an ultrasonic transducer equipped with a lens making it possible to obtain an annular focus from a transducer with a spherical geometry. This particular construction makes it possible to widen the focal area to the size of the ring, but it also causes an overlap area to appear situated on the central axis of the transducer resulting from the intersection of the ultrasonic beams beyond the focal plane of the transducer. This document provides a system for reducing the pressure field and that overlap area so as to eliminate the risk of secondary lesions.

Document XP 55009820 describes a therapeutic probe including an emission surface of revolution created by the rotation around an axis of symmetry of a concave curve segment whereof the center of curvature is located away from the axis of symmetry. This emission surface has, in a profile plane, two concave curve segments that are symmetrical relative to the axis of symmetry, with each concave curve segment having an acoustic axis passing through the center of curvature and the middle of the concave curve segment.

Such a transducer on the one hand makes it possible to obtain a ring for focusing the ultrasonic waves delimited by the focal plane, and on the other hand to obtain an area of intersection of the ultrasonic beams. As clearly emerges from this document, the area of intersection of the ultrasonic beams that corresponds to the secondary pressure peak is situated behind the focal plane.

Document US 2009/230823 describes a therapeutic probe including a transducer having a spherical emission surface including series of ultrasonic transmitters that can be sought out independently. The groups of transducers are oriented to target a common focal point. Insofar as the transducers are co-focal, the axes of the acoustic transducers are focused on a single point.

The present invention aims to resolve the drawbacks of the various prior technical solutions by proposing a new therapeutic probe suitable for obtaining a relatively high volume of biological lesions while preserving the adjacent biological areas not requiring treatment using ultrasonic waves.

To achieve such an aim, the therapeutic probe for treating tissue using focused ultrasonic waves includes a transducer formed by a plurality of ultrasonic sources distributed over an emission surface to focus the ultrasonic waves into a first focal area established in a focal plane, the emission surface having, within a profile plane, two concave curve segments which have a finite length, and which are symmetrical relative to a plane of symmetry or to an axis of symmetry, each concave curve segment has an acoustic axis passing through the center of curvature and the middle of said concave curve segment, said emission surface being created either by rotating one of the concave curve segments around the axis of symmetry or by translating both curve segments in a direction perpendicular to the profile plane containing said curve segments.

According to the invention:
  within the profile plane, the two concave curve segments follow arcs of first and second non-coincident circles that intersect each other, one of the concave curve segments following the arc of the first circle with that arc that is situated within the second circle, while the other of the two concave curve segments following the arc of the second circle, with the arc being situated inside the first circle,
  each curve segment has an acoustic axis intersecting the axis of symmetry or the plane of symmetry between the first focal area and the emission surface, the acoustic axes being separated from each other, at the first focal area, by a separating distance comprised between 1 and 50 mm, such that the beams of the emission surface intersect to create a second focal area that is located and situated between the first focal area and the emission surface, and separated from the focal plane, the emission surface includes an inner edge whereof the symmetrical parts extending on either side of the axis of symmetry or plane of symmetry are separated from each other by an inner distance comprised between 10 and 120 mm allowing the second focal area to be positioned away from the emission surface.

Furthermore, the therapeutic probe according to the invention may furthermore have, in combination, one and/or another of the following additional features:
the emission surface includes an outer edge whereof the symmetrical parts extending on either side of the axis of symmetry [or] plane of symmetry are separated from each other by an outer distance comprised between 30 and 300 mm,
the inner edge delimits, in the emission surface, a housing for mounting an ultrasonic imaging probe,
each concave curve segment is a concave arc of circle segment,
the emission surface results from a toroid geometry created by rotating one of the concave curve segments around the axis of symmetry such that the first focal area has a crown shape,
the emission surface is truncated symmetrically relative to the axis of symmetry,
the emission surface results from a cylindrical geometry created by translating both curve segments over a finite length in a direction perpendicular to the profile plane containing said curve segments, such that the first focal area has a dual linear shape.

The invention also relates to a therapeutic apparatus for treating tissue by emitting focused ultrasonic waves, including a therapeutic probe whereof the ultrasonic sources are activated by signals delivered by a signal generator that is part of a control circuit, so as to focus the ultrasonic waves in a first focal area and obtain a second focal area located and situated between the first focal area and the emission surface.

Various other features will emerge from the description provided below in reference to the appended drawings, which show, as non-limiting examples, embodiments of the subject-matter of the invention.

Figure 1:
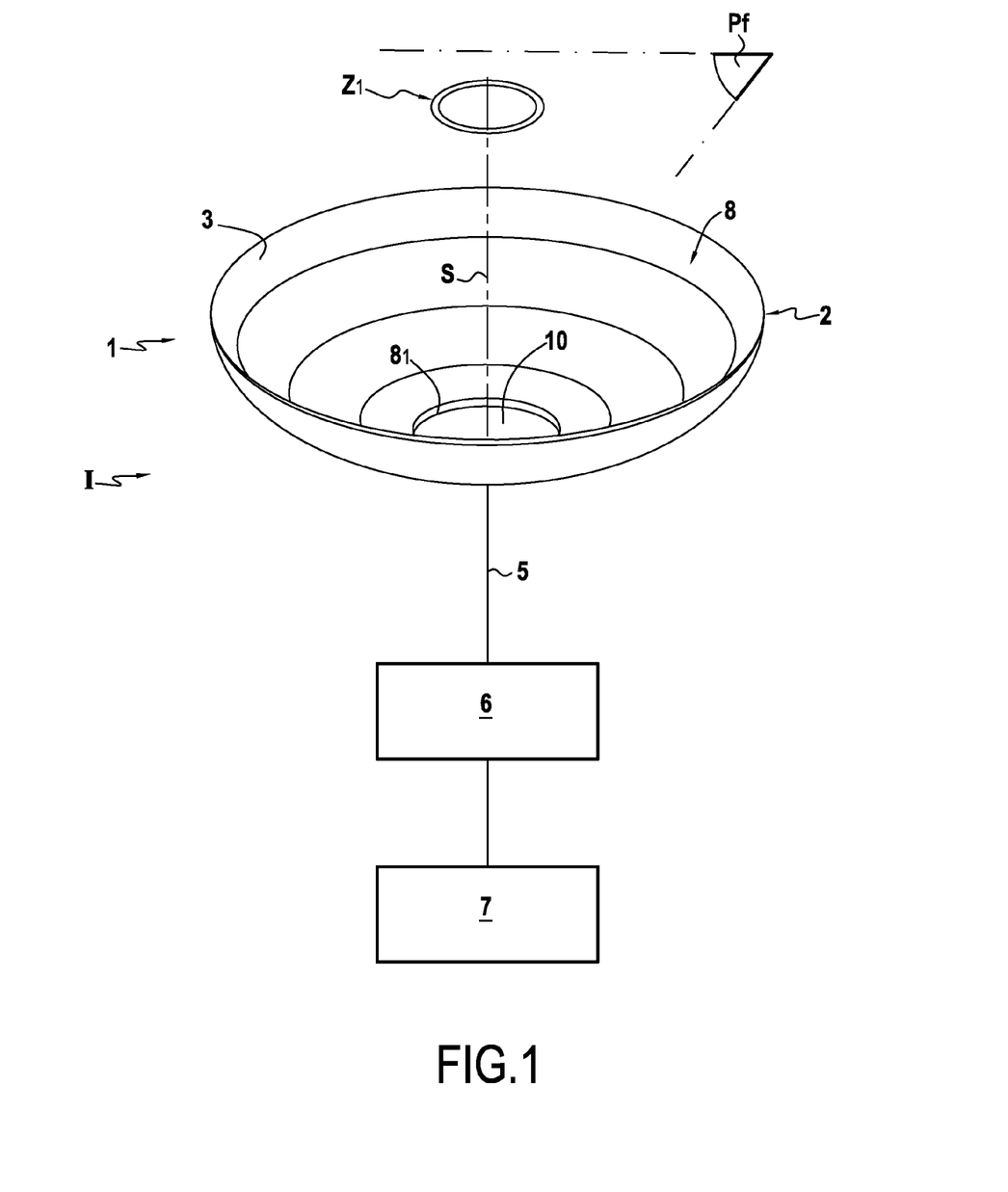
FIG. 1 is a block diagram of the therapeutic probe according to the invention.

As emerges more specifically from FIG. 1, the subject-matter of the invention relates to a therapeutic probe 1 that is part of a therapeutic apparatus I within the general meaning suitable for treating the tissue of a living being using high-intensity focused ultrasounds (HIFU). The therapeutic probe 1 in particular includes a transducer 2 including one or more ultrasonic sources 3, for example such as piezoelectric elements. These ultrasonic sources 3 are connected by means of coaxial cables 5 via an amplifier stage 6 to a control circuit 7 delivering signals to activate the ultrasonic sources 3. The control circuit 7 is not more specifically described, as its production is part of the technical knowledge of those skilled in the art. This control circuit 7 thus traditionally includes a control signal generator that is connected to the ultrasonic sources by means of the amplifier stage 6.

The transducer 2 has a surface 8 for emitting focused ultrasonic waves in a first focal plane $Z_1$, the geometry of which depends on the shape of the emission surface of the ultrasonic transducer.

Figure 2:
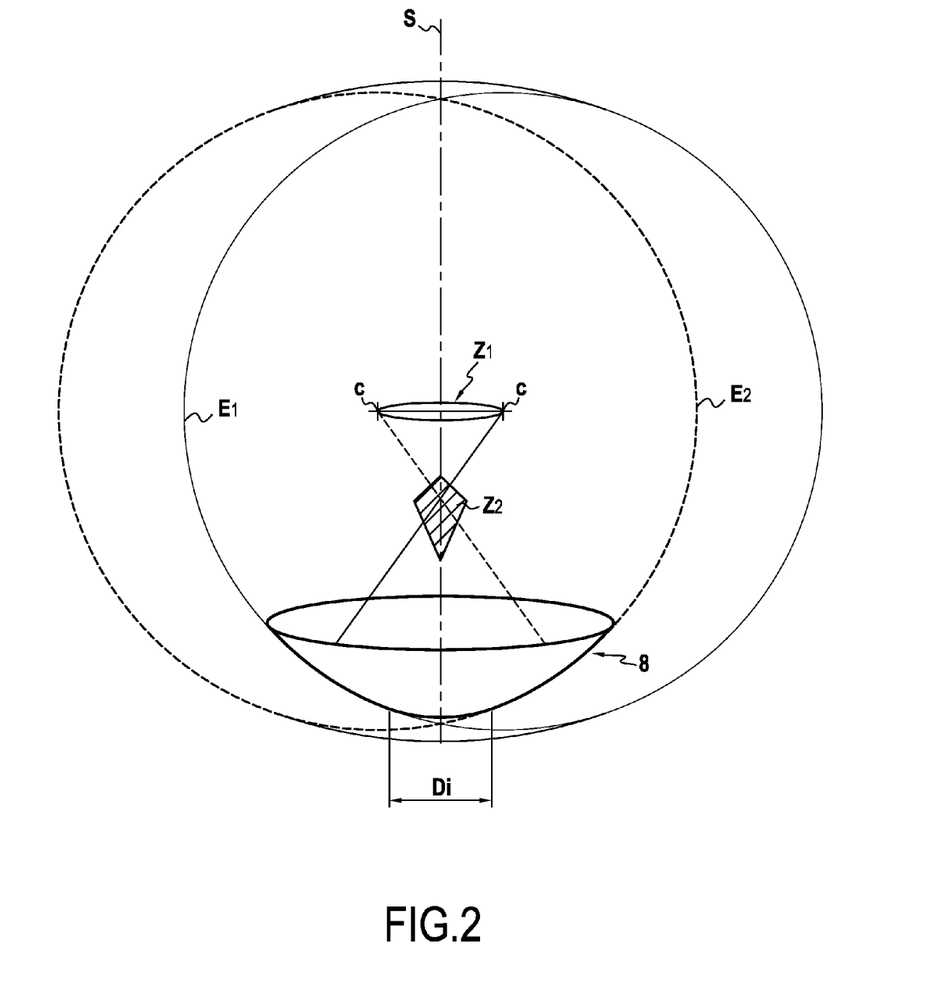
FIG. 2 is a perspective view of a toroid therapeutic probe according to the invention.
Figure 2A:
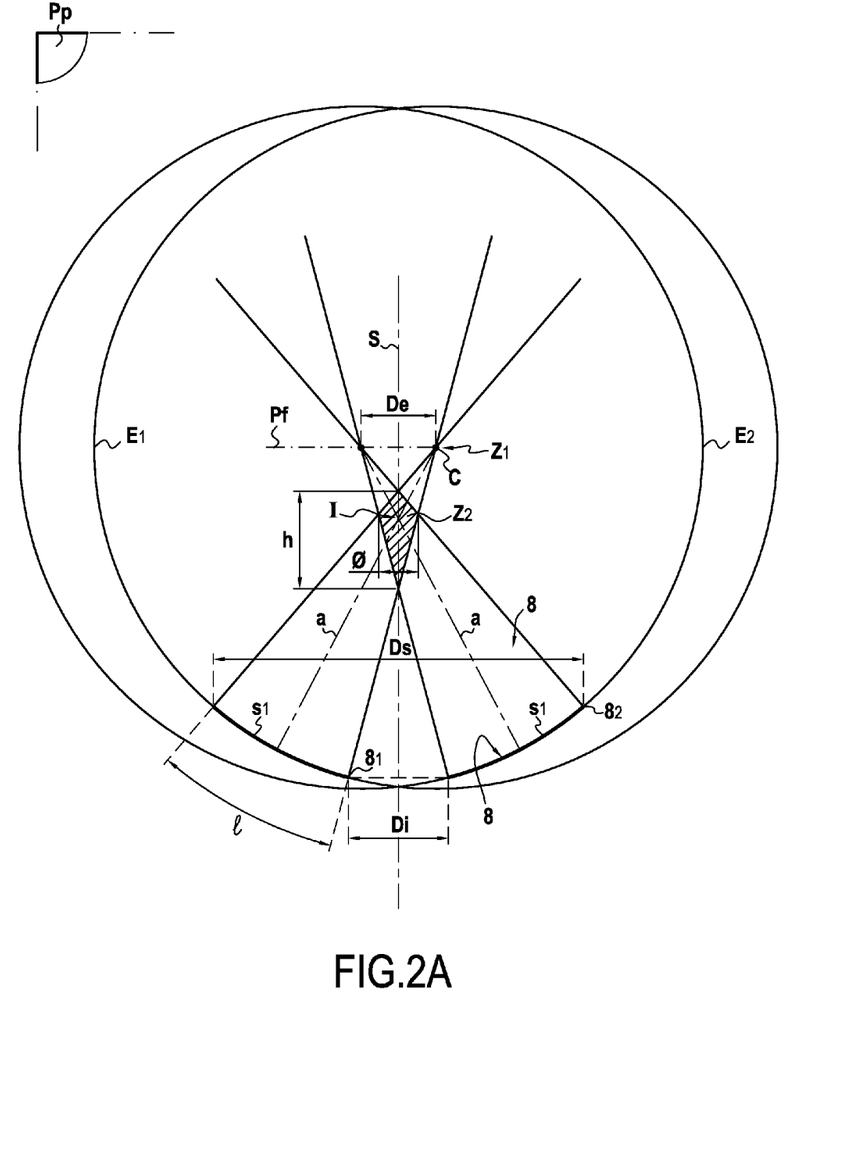
FIG. 2A is an elevation cross-sectional view of the toroid therapeutic probe according to the invention illustrated in FIG. 2.
Figure 3:
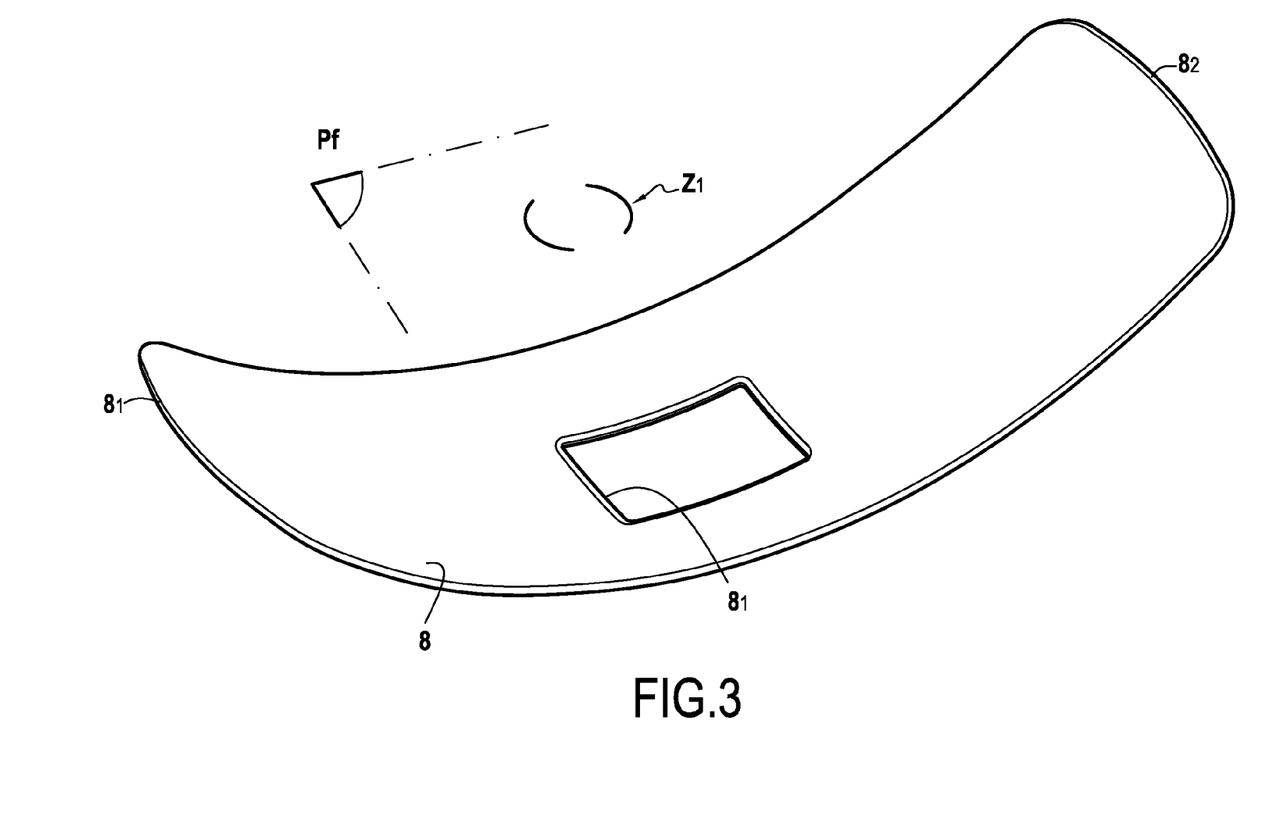
FIG. 3 is a perspective view of a truncated toroid therapeutic probe.
Figure 4:
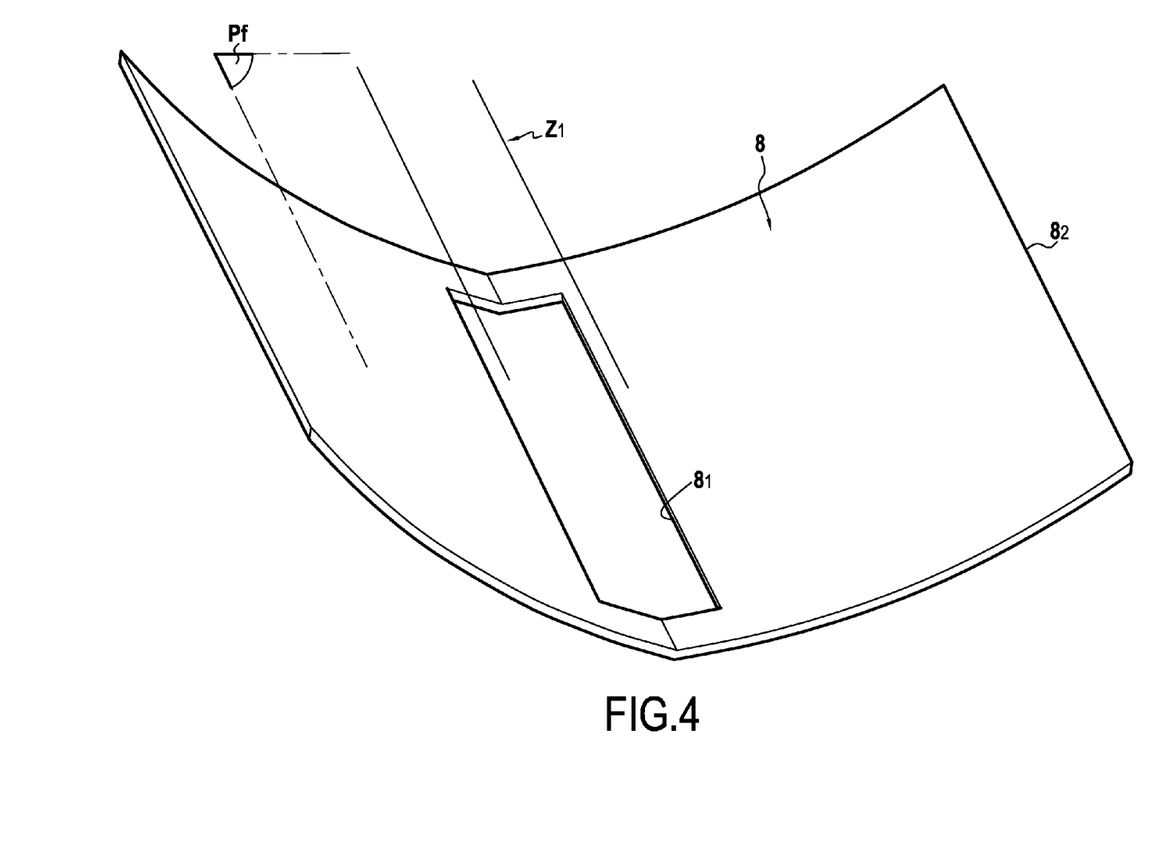
FIG. 4 is a perspective view of a therapeutic probe made up of two cylinder portions.

In the example illustrated in FIGS. 1 to 3, the first focal area $Z_1$ is in the shape of a ring or crown established in a focal plane Pf, while in the example illustrated in FIG. 4, the first focal area $Z_1$ has a dual linear shape established in a focal plane Pf.

In the example embodiment illustrated in FIGS. 1 to 3, the emission surface 8 of the ultrasonic transducer 2 is a surface of revolution generated by the rotation, around an axis of symmetry S, of a concave curve segment $s_1$ of finite length l and having a center of curvature C situated in the focal plane Pf. The center of curvature C is situated on the side opposite said curve segment $s_1$ relative to the axis of symmetry S. Thus, the acoustic or focal axis a passing through the center of curvature C and the middle of the concave curve segment $s_1$ intersects the axis of symmetry S between the focal plane Pf and the emission surface 8. The geometry of said emission surface 8 may be considered to result from an intersected toroid geometry.

As appears clearly in FIGS. 2 and 2A, this emission surface 8 has, in the profile plane Pp, two concave curve segments $s_1$ that are symmetrical relative to the axis of symmetry S. Thus, each concave segment $s_1$ of the emission surface 8 focuses the ultrasonic waves at a point of the first focal area $Z_1$ situated beyond the axis of symmetry S relative to the emission surface 8. Consequently, the curve segment $s_1$ situated on the right in FIG. 2 focuses the ultrasonic wave on the left side of the first focal area $Z_1$ and vice versa.

As emerges from FIGS. 2 and 2A, the emission surface 8 includes, in the profile plane Pp, two concave curve segments $s_1$ that follow the arcs of the first circle $E_1$ having a center C and a second circle $E_2$ having another center C different from the center of the first circle E. The first and second circles $E_1$, $E_2$ do not coincide, but intersect each other. One of the two concave curve segments $s_1$ (on the left in FIGS. 2 and 2A) follows the arc of the first circle $E_1$, said arc of the first circle $E_1$ being situated inside the second circle $E_2$. Similarly, the other of the two concave segments $s_1$ (on the right in FIGS. 2 and 2A) follows the arc of the second circle $E_2$, said arc of the second circle $E_2$ being situated inside the first circle $E_1$.

The preceding description shows that the first focal area $Z_1$ thus has an annular shape with a separating diameter $D_e$. According to one advantageous feature, the acoustic axes a of the two symmetrical curve segments $s_1$ are separated from each other at the focal plane Pf by a separating distance $D_e$ comprised between 1 and 50 mm.

It should be noted that under these conditions, for two parts of the emission surface 8, situated symmetrically relative to the axis of symmetry S, the corresponding acoustic axes a intersect the axis of symmetry S at a shared point of intersection I situated between the first focal area $Z_1$ and the emission surface 8. Thus, the beams of the emission surface 8 intersect to form a second focal area $Z_2$ that is located and situated between the first focal area $Z_1$ and the emission surface 8. The second focal area $Z_2$, which corresponds to an overlap area of the ultrasonic beams, has two characteristic dimensions, i.e., its diameter Ø and its length h (FIG. 2).

According to another feature that more specifically appears in FIG. 1, the emission surface 8 has a cutout or opening 10 centered on the axis of symmetry S. The emission surface 8 thus has an inner edge $8_1$ thereby delimiting the cutout 10. The parts of the inner edge $8_1$ that are symmetrical relative to the axis of symmetry S are separated from each other by an inner distance $D_i$ comprised between 10 and 120 mm. In other words, the parts of the inner edge $8_1$ of two curve segments that are symmetrical relative to the axis of symmetry S are separated from each other by the inner distance $D_i$ making it possible to vary the diameter Ø as well as to position the second focal area $Z_2$ away from the emission surface 8, by varying its length h.

As clearly shown by FIG. 2, the second focal area $Z_2$ is located below the focal plane Pf, thereby making it possible to bring the acoustic energy back between the focal plane Pf of the transducer and its emission surface 8. The second focal area $Z_2$, which corresponds to the overlap area of the ultrasonic waves, is advantageously used to create a large biological lesion.

This technique is counter to the traditional approach, which recommends depositing the acoustic energy away from the transducer, and in particular beyond the focal plane Pf, so as to best preserve the intermediate biological structures situated between the focal plane Pf and the transducer 2. However, the interest of this invention lies in using the overlap area of the beams situated below the focal plane Pf, as the treatment area, and eliminating the intersection of the ultrasonic beams beyond the focal plane that causes uncontrolled secondary lesions with very sharp geometries that are not relevant relative to the geometry of the tissue to be treated. The present invention makes it possible to control the geometry of the lesions produced by combining the first $Z_1$ and second $Z_2$ focal areas.

The dimensions Ø and h of the second focal area $Z_2$ may also be adjusted from the inner distance $D_i$ separating the opposite parts of the inner edge $8_1$. In this respect, it should be noted that the inner edge $8_1$ advantageously delimits a housing for mounting an ultrasonic imaging probe. The outer distance $D_s$ makes it possible to locate the second focal area $Z_2$ away from the focal plane $P_f$. In other words, the second focal area $Z_2$ does not touch the focal plane $P_f$. According to one alternative embodiment, the second focal area $Z_2$ and the first focal area $Z_1$ are distinct from one another, i.e., they are separate.

The dimensions of the second focal area $Z_2$ may also be controlled in particular from the outer distance Ds taken between the parts that are symmetrical relative to the axis of symmetry S, from an outer edge $8_2$ delimiting the periphery of the emission surface 8. Advantageously, the symmetrical parts of the outer edge $8_2$ extending on either side of the axis of symmetry are separated from each other by an outer distance $D_s$ comprised between 30 and 300 mm.

According to one advantageous embodiment of the alternative illustrated in FIGS. 1 and 2, each concave curve segment $s_1$ is a concave arc of circle segment. In the example illustrated in FIGS. 1 and 2, the emission surface 8 is a complete surface of revolution including, for example, a series of ultrasonic transducer elements 3 mounted concentrically relative to one another and relative to the axis of symmetry S. Of course, it may be considered, as illustrated in FIG. 3, for the emission surface 8 to be truncated symmetrically relative to the axis of symmetry S so that the transducer is limited to a portion of an intersected toroid having a length for example comprised between 5 and 250 mm. According to this example embodiment, the transducer 2 has a series of ultrasonic transducer elements 3 mounted concentrically relative to one another and relative to the axis of symmetry S such that they each assume the form of a ring or crown segment.

Figure 5:
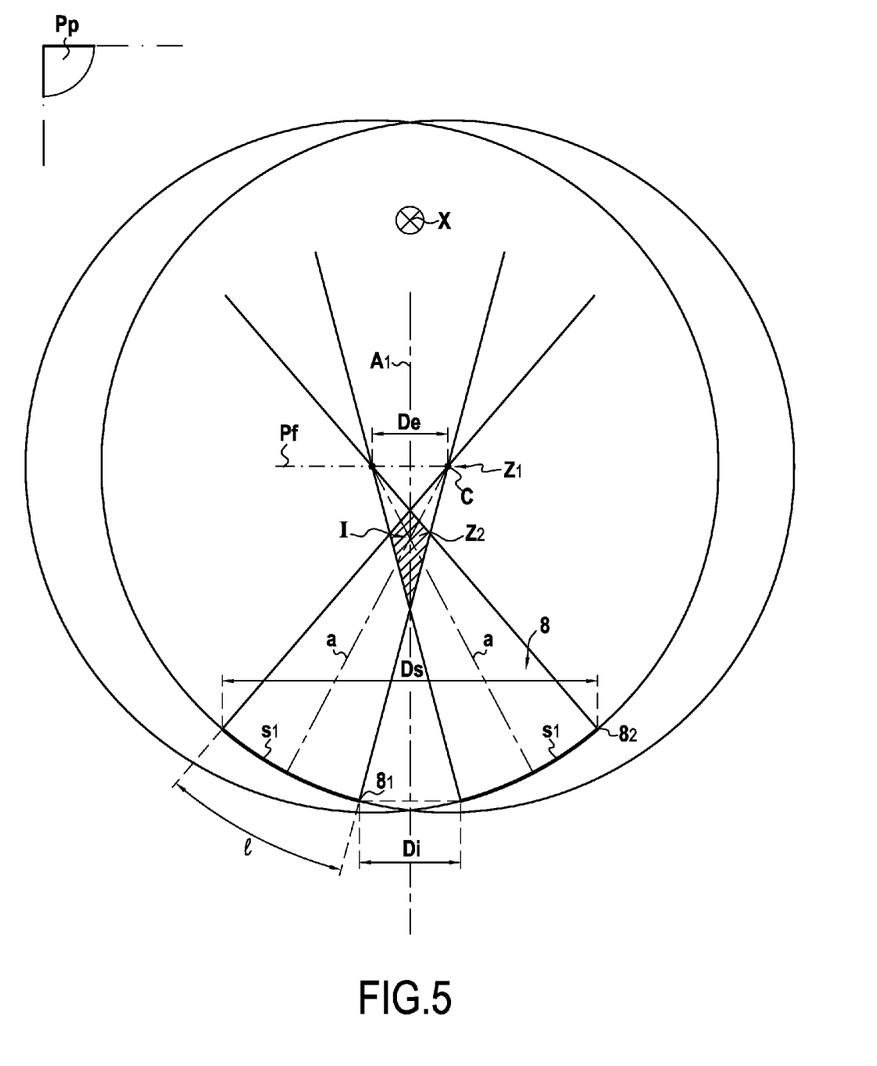
FIG. 5 is an elevation cross-sectional view of the therapeutic probe illustrated in FIG. 4.

FIGS. 4 and 5 illustrate another alternative embodiment of the emission surface 8 in which said emission surface 8 is created by translating two symmetrical curve segments $s_1$, in a direction X perpendicular to the profile plane Pp containing the two curve segments $s_1$. This translation is done in the direction X over a limited length adapted to the desired size of the emission surface 8. According to this alternative embodiment, the emission surface 8 has a pseudo-cylindrical shape, a tubular shape, or a shape made up of two cylinder portions, whereas in the example illustrated in FIGS. 1 and 2, the emission surface 8 is of revolution. However, as shown by comparing FIGS. 2 and 5, the emission surface 8 illustrated in FIGS. 4 and 5 has, in profile, the same geometric characteristics as those described in FIGS. 1 and 2.

Each curve segment $s_1$ has a concave shape and a finite length. The two curve segments $s_1$ are symmetrical relative to a plane of symmetry $A_1$ that is perpendicular to the profile plane Pp. Each curve segment $s_1$ thus has an acoustic axis a intersecting the plane of symmetry $A_1$ between the first focal area $Z_1$ and the emission surface 8. Each curve segment $s_1$ of the emission surface 8 focuses the ultrasonic waves at a point of the first focal area $Z_1$ situated beyond the plane of symmetry $A_1$ relative to the emission surface 8. Consequently, given the plane-type symmetry, the first focal area $Z_1$ has a dual linear shape. In fact, each part of the emission surface 8 focuses, beyond the plane of symmetry $A_1$, along a linear segment extending in the focal plane Pf, parallel to the direction X.

The acoustic axes a of the two symmetrical curve segments s1 are separated at the first focal area $Z_1$ by an inner distance $D_e$ according to the characteristics described above. Likewise, according to this alternative, a second focal area $Z_2$ is created that is located and situated between the first focal area $Z_1$ and the emission surface 8. The second focal area $Z_2$ has the same characteristics as those described relative to FIGS. 1 and 2.

In the preceding description, the emission surface 8 is shown as intrinsically being part of the transducer 2. Of course, it is clear that the emission surface 8 may be formed by the transducer, but also by the surface of a reflector, an acoustic lens, or other means.

The invention claimed is:

1. A therapeutic probe for treating tissue using a transducer for focusing ultrasonic waves and formed by a plurality of ultrasonic sources distributed over an emission surface to focus the ultrasonic waves into a first focal area established in a focal plane situated in front of the transducer, the probe comprising:

the emission surface formed by the transducer with a cross section in a profile plane perpendicular to the focal plane, having, within the profile plane, two concave curve segments which have a finite length, and which are symmetrical relative to an axis of symmetry, or to a plane of symmetry, each concave curve segment having an acoustic axis passing through the center of curvature and the middle of said concave curve segment, said emission surface being created either by rotating one of the concave curve segments around the axis of symmetry such that the emission surface is of revolution, or by translating both concave curve segments in a direction perpendicular to the profile plane containing said concave curve segments such that the emission surface has a shape made up of two cylinder portions, wherein, within the profile plane, the two concave curve segments follow arcs of first and second non-coincident circles that intersect each other, one of the concave curve segments following the arc of the first circle with the arc that is situated within the second circle, while the other of the two concave curve segments following the arc of the second circle, with the arc being situated inside the first circle, wherein the acoustic axis of each concave curve segment intersects the axis of symmetry, or the plane of symmetry, between the first focal area and the emission surface, the acoustic axes being separated from each other, at the first focal area, by a separating distance comprised between 1 and 50 mm, such that the beams of the emission surface intersect to create a second focal area that is located and situated between the first focal area and the emission surface, and separated from the focal plane, wherein the emission surface includes an inner edge, and wherein the symmetrical parts extending on either side of the axis of symmetry, or plane of symmetry, are separated from each other by an inner distance comprised between 10 and 120 mm, allowing the second focal area to be positioned away from the emission surface.

2. The therapeutic probe according to claim 1, wherein the emission surface includes an outer edge wherein the symmetrical parts extending on either side of the axis of symmetry, or plane of symmetry, are separated from each other by an outer distance comprised between 30 and 300 mm.

3. The therapeutic probe according to claim 1, wherein the inner edge delimits, in the emission surface, a housing for mounting an ultrasonic imaging probe.

4. The therapeutic probe according to claim 1, wherein each concave curve segment is a concave arc of a circle segment.

5. The therapeutic probe according to claim 1, wherein each concave curve segment is configured such that translating both curve segments over a finite length in a direction perpendicular to the profile plane containing said concave curve segments results in creating the emission surface, such that the first focal area has a dual linear shape.

6. A therapeutic apparatus for treating tissue by emitting focused ultrasonic waves, including a therapeutic probe according to claim 1, wherein the ultrasonic sources are activated by signals delivered by a signal generator that is part of a control circuit, so as to focus the ultrasonic waves in a first focal area, and obtain a second focal area located and situated between the first focal area and the emission surface.

7. The therapeutic probe according to claim 1, wherein each concave curve segment is configured such that rotating one of the concave curve segments around the axis of symmetry results in creating the emission surface, such that the first focal area has a crown shape.

8. The therapeutic probe according to claim 7, wherein the emission surface is truncated symmetrically relative to the axis of symmetry.

* * * * *